(12) United States Patent
Jin et al.

(10) Patent No.: US 12,331,365 B2
(45) Date of Patent: Jun. 17, 2025

(54) ADENOSINE TRIPHOSPHATASE SARCOPLASMIC/ENDOPLASMIC RETICULUM Ca2+ TRANSPORTING 2 (ATP2A2) GENE-BASED MOLECULAR MARKER FOR IDENTIFYING CHICKEN FEED EFFICIENCY TRAIT, AND IDENTIFICATION METHOD AND USE THEREOF

(71) Applicant: Anhui Agricultural University, Hefei (CN)

(72) Inventors: Sihua Jin, Hefei (CN); Yuanfei Ding, Hefei (CN); Zhaoyu Geng, Hefei (CN); Yi Fang, Hefei (CN); Xin Wang, Hefei (CN); Xiaoqing Hu, Hefei (CN); Xin Wang, Hefei (CN); Xuling Liu, Hefei (CN); Xing Liu, Hefei (CN); Yiran Luo, Hefei (CN); Lu Feng, Hefei (CN); Dehua Zha, Hefei (CN)

(73) Assignee: Anhui Agricultural University, Hefei (CN)

( * ) Notice: Subject to any disclaimer, the term of this patent is extended or adjusted under 35 U.S.C. 154(b) by 0 days.

(21) Appl. No.: 18/672,154

(22) Filed: May 23, 2024

(65) Prior Publication Data

US 2025/0043365 A1 Feb. 6, 2025

(30) Foreign Application Priority Data

May 23, 2023 (CN) .......................... 202310596686.4

(51) Int. Cl.
| | | |
|---|---|---|
| *C12P 19/34* | (2006.01) | |
| *C12Q 1/44* | (2006.01) | |
| *C12Q 1/6806* | (2018.01) | |
| *C12Q 1/686* | (2018.01) | |
| *C12Q 1/6888* | (2018.01) | |
| *G01N 27/447* | (2006.01) | |

(52) U.S. Cl.
CPC ............ *C12Q 1/6888* (2013.01); *C12Q 1/44* (2013.01); *C12Q 1/6806* (2013.01); *C12Q 1/686* (2013.01); *G01N 27/44726* (2013.01); *C12Q 2600/124* (2013.01); *G01N 2333/916* (2013.01)

(58) Field of Classification Search
CPC .................................................. C12Q 1/6888
See application file for complete search history.

(56) References Cited

U.S. PATENT DOCUMENTS

2016/0326601 A1* 11/2016 Hu ........................ C12Q 1/6888

OTHER PUBLICATIONS

Xiao et al., Frontiers in Genetics 12:607719 (2021) (Year: 2021).*
Yang et al., BMC Genomics 21(1), 292 (2020) (Year: 2020).*
Chinese First Office Action with English Translation, Application No. 202310596686.4, Applicant: Agricultural University of Anhui, Title: Molecular Marker for Identification of Chicken Feed Utilization Trait Based on ATP2A2, Dated: Mar. 21, 2024.
Chinese Notification to Grant Patent Right for Invention, Application No. 202310596686.4, Issue No. 2024040800084380, Applicant: Agricultural University of Anhui, Title: Molecular Marker for Identification of Chicken Feed Utilization Trait Based on ATP2A2, Dated: Apr. 8, 2024.
www.nature.com/scientificreports, Scientific Reports; An Integrative Transcriptome analysis indicates regulatory mRNA-miRNA networks for Residual Feed Intake in Nelore cattle, Authors; Priscilla S. N. De Oliveria, et al., Published online: Nov. 20, 2018.
BMC Genomics, Research Article; Messenger RNA sequencing and pathway analysis provide novel insights into the biological basis of chickens' feed efficiency, Authors: Nan Zhou, et al., BMC Genomics (2015) 16:195, DOI10.1186/s12864-015-1364-0, pp. 1-20.
http://feb2023.archive.ensembl.org/Gallus_gallus_GCA_000002315.5/Variation/Sequence?db-core;r-15:5642411;v rs317648351;vdb-variation;vf24019362, Chicken (Red Jungle fowl)(GRCg6a), Flanking sequence.

* cited by examiner

*Primary Examiner* — Kenneth R Horlick
(74) *Attorney, Agent, or Firm* — Reising Ethington P.C.

(57) ABSTRACT

An adenosine triphosphatase sarcoplasmic/endoplasmic reticulum $Ca^{2+}$ transporting 2 (ATP2A2) gene-based molecular marker is provided for identifying a chicken feed efficiency trait, and an identification method and use thereof. A nucleotide sequence of the molecular marker is shown in SEQ ID NO: 1, and a base at locus 926 in the nucleotide sequence is T or G. In the present application, by identifying a genotype of the molecular marker in a chicken genome and then selecting the chicken feed efficiency trait according to the genotype, a breeding method for early selection of the poultry feed efficiency trait is established.

3 Claims, 2 Drawing Sheets

Specification includes a Sequence Listing.

SEQUENCE LISTING

```
Sequence total quantity: 7
SEQ ID NO: 1           moltype = DNA  length = 2000
FEATURE                Location/Qualifiers
source                 1..2000
                       mol_type = genomic DNA
                       note = molecular marker located in a promoter region of an
                       ATP2A2 gene
                       organism = Gallus sp.
SEQUENCE: 1
tctgttttca atggataaga gagaaacaag gaaagtggag ctgtcaagct gtagcagaac   60
tagtgaatcc tagagaatgc caagagttca ccaagattag gtagaatgca aactctacct  120
tcctagcaac atttctgcct gttaaccagt cggactactt ttttttttata cactgccaac  180
ctctaattgc acatgccatg gttctggtat gcctaaaatac ttttctgtaa gccttttttgg  240
```

```
aaacaagctc aaaaaggaaa ccaataatga catacagagt acataacaga aggaaataac     300
tatgaaacat gacagttttg gggtttgttt ttttttttt tgttacagtt agagcatatc      360
tacatgtgtg cagtgtgatg cagtgatccg agaagcaacg taactgtatt caagtaacat    420
ttgggcacac agactaacct gtctaataat aaaggataaa attatatgg gcatggagta     480
actaattctc gtacctaaac tgggtcatca gatctaactc atgattttt gttcaggact      540
gtcccgtgaa gcgcagacat gctgtcaaga agcccttacc tggacactgg ctaattacac    600
aggaatctct tctggggcag ctgcactttt gctagaaagg atgcagggca acacagcacc    660
taggatgcca tattttatat cgctgtcccc tctcctcact tcctttgcca gtacagaggt    720
aagattaaga tattttcctt ccagatcagt ttctcacagt gtgatactgt gggtggtttt     780
tagcagcgat ggatgtgcag cttgtatgta ggatctgcat ttatgtaagc cagcacacat    840
gaacagatca gctcttgtat ttgcacatgc ataagagctg gttgaaacca agtgcttta     900
agggaattta tactgtgctc tgtactgttt gctattgctg gtgacattgc tggtgtcact    960
gatgtcagac ggtgctgatc taacagctca tactgcattc attgaagtct ctgtgaatta   1020
aggggtagga tggctaaatc agtctgtttt cagcattctg tgtctgtttt tgagtctctca  1080
ccacttacgg agatgctgcg ctgagggaag ctgctatctc acaccacgca cactgctgaa   1140
atcacactgt gcagttcata cctcctcgcg ttatcaccgt gcaagccagg gctgagtgtg   1200
cgtgtcactg ttatgctggc aggggcagcg tgcggcgcag cgggaattgg ggaagtcgtg   1260
tgaaagacac ggctgtgcca gcacaggccc cgcacagccc agcgggacct ctggggaacg   1320
aaccccctctg gtgccggcag ggaggcacgt agccgcgctt cctatcctcg ccctggcg    1380
atccgtggcg gggtgaggct cctgtcctca cagtacagcc cctcaactca cccttttgcct  1440
gttttttgtc acgactgagg tggcggcagc ccagccctcg ctggccgttt acgtgaggtt   1500
cctgtcacga ctgaggtggc ggtagcccta ccctcactgt ttggccgttt atgtgaggtt   1560
cctgtcacga cagagccggg cagccccaca cgcgcgctcc aggctcgcat tcctgtcacc   1620
gagcgcgctc ccctcagccg gggcagcccc gcttccctct gccactctgc gcgggttgaa   1680
gccgggacag agggcggcca cagcggttca ctccggggcca ggggggcggg aaagcggcca   1740
ccccacctgc aggcctctcc cacggcggag cggaagcgct cgaccggcca cacgaggcct   1800
gcatcacccct ccgcctcctc ctcctccacc cctcagccga gggcgggcga ccgcgctgcg   1860
caggaccgcg cctcagcgcc gtgggcgtg gcccgctct gttccgcccc ctcctctggg    1920
tcggccaatc agcggcgtcc acatgccgcg gcggtgagtg ggcccccgg cggcccagct    1980
cccgtaagtt acattagagc                                                2000

SEQ ID NO: 2          moltype = DNA   length = 18
FEATURE               Location/Qualifiers
source                1..18
                      mol_type = other DNA
                      note = forward primer for specific amplification
                      organism = synthetic construct
SEQUENCE: 2
tttagcagcg atggatgt                                                   18

SEQ ID NO: 3          moltype = DNA   length = 18
FEATURE               Location/Qualifiers
source                1..18
                      mol_type = other DNA
                      note = reverse primer for specific amplification
                      organism = synthetic construct
SEQUENCE: 3
gcgaggaggt atgaactg                                                   18

SEQ ID NO: 4          moltype = DNA   length = 391
FEATURE               Location/Qualifiers
source                1..391
                      mol_type = genomic DNA
                      note = sequence of amplified region for the primers
                      organism = Gallus sp.
SEQUENCE: 4
tttagcagcg atggatgtgc agcttgtatg taggatctgc atttatgtaa gccagcacac     60
atgaacagat cagctcttgt atttgcacat gcataagagc tggttgaaac caagtgcttt    120
taagggaatt tatactgtgc tctgtactgt ttgctattgc tggtgacatt gctggtgtca    180
ctgatgtcag acggtgctga tctaacagct catactgcat tcattgaagt ctctgtgaat    240
taaggggtag gatggctaaa tcagtctgtt ttcagcattc tgtgtctgtt tttgagtctc    300
tgccacttac ggagatgctg cgctgaggga agctgctatc tcacaccacg cacactgctg    360
aaatcacact gtgcagttca tacctcctcg c                                    391

SEQ ID NO: 5          moltype = DNA   length = 10
FEATURE               Location/Qualifiers
source                1..10
                      mol_type = genomic DNA
                      note = sequencing result of genotype verification for locus
                       926
                      organism = Gallus sp.
SEQUENCE: 5
tgtactgttt                                                            10

SEQ ID NO: 6          moltype = DNA   length = 10
FEATURE               Location/Qualifiers
```

```
source                  1..10
                        mol_type = genomic DNA
                        note = sequencing result of genotype verification for locus
                        926
                        organism = Gallus sp.
SEQUENCE: 6
tgtacggttt                                                                        10

SEQ ID NO: 7            moltype = DNA   length = 10
FEATURE                 Location/Qualifiers
source                  1..10
                        mol_type = genomic DNA
                        note = sequencing result of genotype verification for locus
                        926
                        organism = Gallus sp.
SEQUENCE: 7
tgtacggttt                                                                        10
```

ADENOSINE TRIPHOSPHATASE SARCOPLASMIC/ENDOPLASMIC RETICULUM Ca2+ TRANSPORTING 2 (ATP2A2) GENE-BASED MOLECULAR MARKER FOR IDENTIFYING CHICKEN FEED EFFICIENCY TRAIT, AND IDENTIFICATION METHOD AND USE THEREOF

CROSS-REFERENCE TO RELATED APPLICATION

This patent application claims the benefit and priority of Chinese Patent Application No. 202310596686.4 filed with the China National Intellectual Property Administration on May 23, 2023, the disclosure of which is incorporated by reference herein in its entirety as part of the present application.

REFERENCE TO SEQUENCE LISTING

A computer readable XML file entitled "GWP20240503322-sequence listing", which was created on Jul. 2, 2024, with a file size of about 11,018 bytes, contains the sequence listing for this application, has been filed with this application, and is hereby incorporated by reference in its entirety.

TECHNICAL FIELD

The present disclosure belongs to the technical field of molecular markers, and in particular relates to an adenosine triphosphatase sarcoplasmic/endoplasmic reticulum $Ca^{2+}$ transporting 2 (ATP2A2) gene-based molecular marker for identifying chicken feed efficiency trait, and an identification method and use thereof.

BACKGROUND

Feed efficiency traits are one of the most important economic traits in livestock production. A feed conversion ratio is an important index to measure feed efficiency. Residual feed intake (RFI) refers to a difference between an actual feed intake and an expected feed intake to maintain the growth needs for animals. RFI is an important index to measure feed conversion ratio. The lower the RFI, the higher the feed conversion ratio. RFI is a medium-to-high genetic trait independent of important growth traits such as an animal body weight and can improve feed efficiency without affecting the growth, fattening, and reproductive performance of livestock. There are many factors affecting RFI, and genetic factors are one of the most important factors affecting the RFI of livestock.

Adenosine triphosphatase sarcoplasmic/endoplasmic reticulum $Ca^{2+}$ transporting 2 (ATP2A2) is one of the members of the ATP2A gene family. De et al. reported that, among mRNA-miRNAs for regulating RFI in Nelore cattle, differentially expressed genes are related to biological processes in animals such as lipid and fatty acid metabolism, energy and growth, xenobiotic metabolism, and oxidative stress, indicating that the ATP2A2 gene is up-regulated in a high feed efficiency group (De Oliveira P S N, Coutinho L L, Tizioto P C, et al. An integrative transcriptome analysis indicates regulatory mRNA-miRNA networks for residual feed intake in Nelore cattle [J].Sci Rep, 2018, 8 (1): 17072-17084). Zhou et al. conducted a transcriptome study on pectoral muscles of broilers in high and low feed efficiency groups. Study results showed that an expression level of the differentially expressed gene ATP2A2 in pectoral muscles of broilers in a high feed efficiency group is higher than an expression level of the differentially expressed gene ATP2A2 in pectoral muscles of broilers in a low feed efficiency group, revealing that the ATP2A2 gene can maintain the energy required for the growth and development of an animal by increasing a $Ca^{2+}$ concentration in the animal (Zhou N, Lee W R, Abasht B.Messenger RNA sequencing and pathway analysis provide novel insights into the biological basis of chickens' feed efficiency [J]. BMC Genomics, 2015, 16 (1): 195-215).

Therefore, the ATP2A2 gene may be an important candidate gene affecting chicken feed efficiency. In order to accurately select a genotype suitable for growth and development and thus provide data for early selective breeding, based on the above content, the present disclosure provides an ATP2A2 gene-based molecular marker for identifying a chicken feed efficiency trait, and an identification method and use thereof.

SUMMARY

An objective of the present disclosure is to provide an ATP2A2 gene-based molecular marker for identifying a chicken feed efficiency trait, and an identification method and use thereof. Compared with the prior art, the present disclosure develops a single nucleotide polymorphism (SNP) molecular marker for a candidate gene (the ATP2A2 gene) related to the chicken feed efficiency trait to solve the problem of slow progress in conventional phenotypic selective breeding and allow the early identification of a feed efficiency trait.

The present disclosure adopts the following technical solutions to achieve the above objective:

An ATP2A2 gene-based molecular marker for identifying a chicken feed efficiency trait is provided, where the molecular marker is located in a promoter region of an ATP2A2 gene and has a nucleotide sequence shown in SEQ ID NO: 1, and a base at locus 926 in the nucleotide sequence is T or G.

A use of the ATP2A2 gene-based molecular marker for identifying a chicken feed efficiency trait in identification of a chicken feed efficiency trait is provided.

A method for identifying a chicken feed efficiency trait using the molecular marker is provided, including the following steps:
(1) extracting total DNA from venous blood of a chicken wing;
(2) designing specific amplification primers with a sequence including a locus at which the molecular marker is located and upstream and downstream bases thereof as a target sequence, and using the specific amplification primers to conduct PCR amplification with the total DNA as a template to obtain an amplification product;
(3) genotyping and sequencing the amplification product to obtain a molecular marker type of a chicken to be tested; and
(4) determining the chicken feed efficiency trait based on the molecular marker type.

As a further optimized solution of the present disclosure, sequences of the specific amplification primers are as follows:

```
SEQ ID NO: 2:
forward primer:
TTTAGCAGCGATGGATGT;
and

SEQ ID NO: 3:
reverse primer:
GCGAGGAGGTATGAACTG.
```

As a further optimized solution of the present disclosure, a method of the genotyping is as follows: cleaving the amplification product with a TatI restriction endonuclease to obtain a cleavage product, detecting the cleavage product by agarose gel electrophoresis, and allowing the genotyping according to an electrophoresis pattern, where if the cleavage product includes:

1 band, then the chicken feed efficiency trait is of a GG genotype;
2 bands, then a TT genotype; and
3 bands, then the chicken feed efficiency trait is of a TG genotype.

As a further optimized solution of the present disclosure, if the molecular marker type of the chicken to be tested is the GG genotype, the chicken feed efficiency trait is at a high level; if the molecular marker type of the chicken to be tested is the TT genotype, the chicken feed efficiency trait is at a low level; and if the molecular marker type of the chicken to be tested is the TG genotype, the chicken feed efficiency trait is at a medium level.

As a further optimized solution of the present disclosure, the cleavage product is detected by agarose gel electrophoresis with a concentration of 2.0% or more.

The present disclosure has the following beneficial effects:

In the present disclosure, by identifying a genotype of the molecular marker in a chicken genome and then selecting the chicken feed efficiency trait according to the genotype, a breeding method for early selection of the chicken feed efficiency trait is established. The method is simple, rapid, and low-cost, does not require special instruments, and is suitable for the needs of marker-assisted selection experiments.

DETAILED DESCRIPTION OF THE EMBODIMENTS

The present application will be described in further detail below with reference to the accompanying drawings. It should be pointed out herein that the following specific implementations are only intended to further explain the present application, rather than to be construed as limiting the protection scope of the present application. Those skilled in the art may make non-essential improvements and adjustments to the present application based on the above content.

1. Materials

All methods used in this embodiment are conventional methods known to those skilled in the art, unless otherwise specified. All materials and reagents used in this embodiment are commercially available, unless otherwise specified.

2. Methods 2.1 Primer Design

DNA sequence corresponding to a promoter of the ATP2A2 gene was found from a chicken genome database, and specific amplification primers were designed with a partial DNA sequence of a promoter region of the ATP2A2 gene (a sequence including a locus at which the polymorphic molecular marker of the present disclosure was located and upstream and downstream bases thereof) as a template. The partial DNA sequence of the promoter region of the ATP2A2 gene is shown in SEQ ID NO: 1. Sequences of the specific amplification primers were as follows:

```
SEQ ID NO: 2:
forward primer:
TTTAGCAGCGATGGATGT;
and

SEQ ID NO: 3:
reverse primer:
GCGAGGAGGTATGAACTG.
```

The amplified region of the primers had a length of 391 bp and a sequence shown in SEQ ID NO: 4, and included a molecular marker with a T/C mutation at locus 926 and a sequence shown in SEQ ID NO: 1.

2.2 Extraction of Total DNA from Blood 468 local roosters (Wannan three-yellow chicken) were selected, venous blood was collected from wings, and total DNA was extracted from the venous blood. The total DNA in a venous blood sample of a chicken wing was extracted using a blood DNA extraction kit produced by TIANGEN, and extraction steps were carried out according to instructions of the kit.

2.3 PCR Amplification

The synthesized sequencing-specific primers were used to conduct the PCR amplification of the target fragment of the ATP2A2 gene with the Mix produced by Yeasen Biotechnology (Shanghai) Co., Ltd., and a PCR amplification system is shown in Table 1:

TABLE 1

| PCR amplification system | |
|---|---|
| Component | Volume |
| DNA template | 0.8 µL |
| Forward primer | 0.1 µL |
| Reveres primer | 0.1 µL |
| Mix | 7 µL |
| ddH$_2$O | 7 µL |
| Total | 15 µL |

PCR conditions were as follows: pre-denaturation at 95° C. for 5 min; step 1: denaturation at 95° C. for 45 s; step 2: annealing at 53° C. to 54° C. for 45 s (a temperature of the annealing was set according to the primers); step 3: extension at 72° C. for 30 s, where steps 2 and 3 were cycled 31 times, with a total of 32 cycles; and extension at 72° C. for 10 min.

2.4 Detection and Sequencing of PCR Amplification Products

Figure 1:
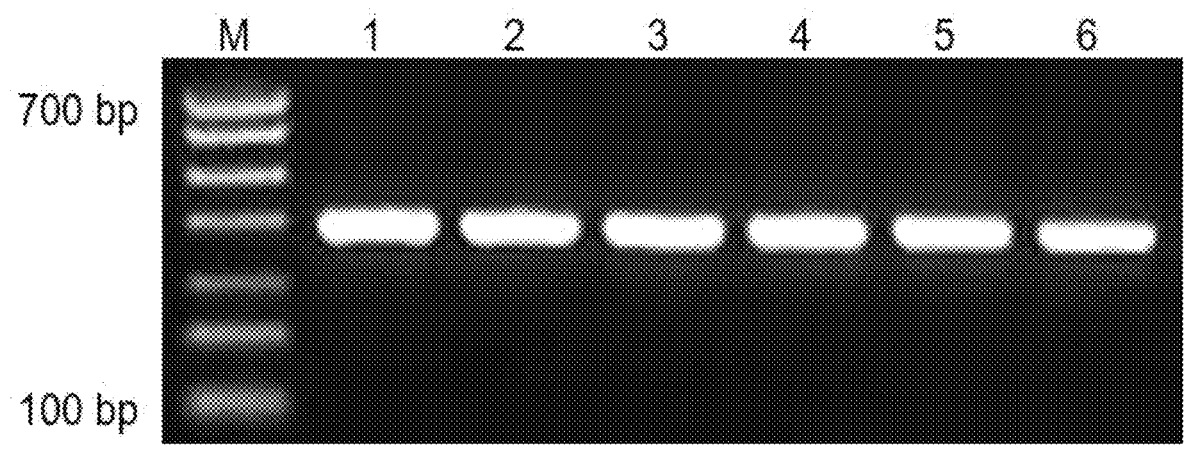
FIG. 1 is an agarose gel electrophoresis pattern of PCR amplification products of some samples.

A PCR amplification product was detected by agarose gel electrophoresis with a mass ratio of 2%, and results are shown in FIG. 1. After imaging on a gel imager, a band with a length of approximately 391 bp was obtained, and this length was consistent with the predicted length, indicating that the target fragment was obtained. The PCR product was sent to Beijing Tsingke Biotechnology Co., Ltd. (Nanjing) for sequencing, and a sequence of the PCR product was shown in SEQ ID NO: 4, which was consistent with the predicted result.

2.5 Genotyping 2.5.1 An enzyme cleavage system shown in Table 2 was prepared. The PCR amplification product was cleaved with a Tat I restriction endonuclease of Thermo Fisher Scientific in a 65° C. water bath for 2 h.

TABLE 2

| Enzyme cleavage system | |
| --- | --- |
| Component | Volume |
| PCR amplification product | 2 μL |
| Tat I | 1 μL (2 U/μL) |
| buffer | 1 μL |
| ddH$_2$O | 6 μL |
| Total | 10 μL |

Figure 2:
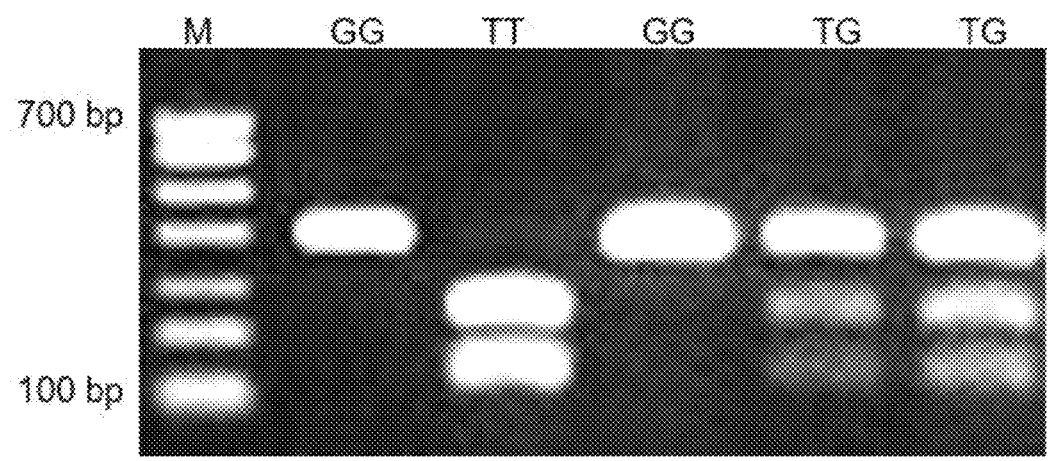
FIG. 2 is an agarose gel electrophoresis pattern of cleavage products resulting from enzyme cleavage of PCR amplification products of some samples.

2.5.2 The cleavage product was detected by low-voltage agarose gel electrophoresis with a mass ratio of 2%, and results are shown in FIG. 2 (partial results). If the cleavage product: included 1 band, it indicated a GG genotype; included 2 bands, it indicated a TT genotype; and included 3 bands, it indicated a TG genotype.

2.6 Enzyme Cleavage Sequencing Verification

Figure 3:
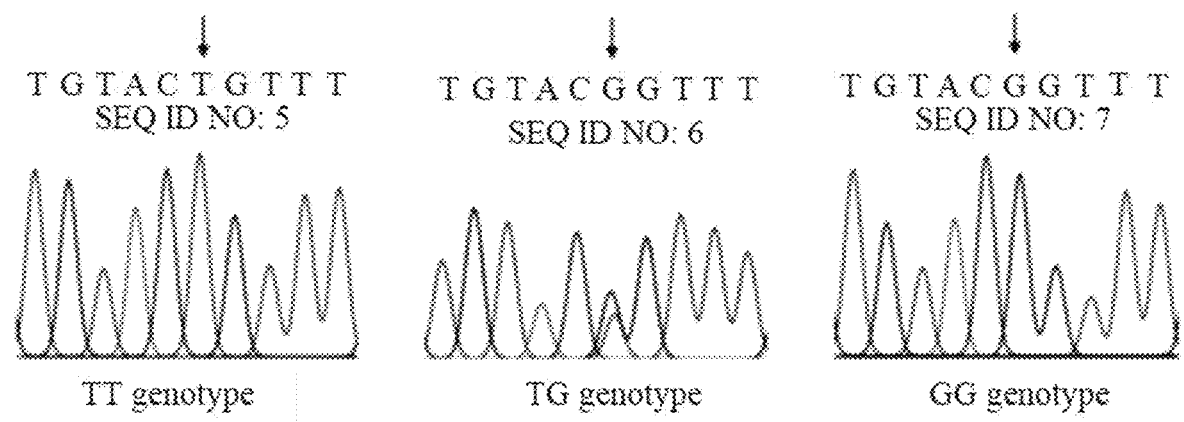
FIG. 3 shows sequencing results of genotype verification for locus 926 (locus 926 in SEQ ID NO: 1) in a promoter region of the ATP2A2 gene in chicken.

According to the agarose gel electrophoresis pattern of enzyme cleavage-based genotyping, the three genotypes of TT, TG, and GG were obtained. One individual was selected from each of the three genotypes for sequence alignment, and sequence alignment results are shown in FIG. 3. In the sequencing results, T was mutated into C, and the arrow marked the mutation locus, which was consistent with the enzyme cleavage-based genotyping result.

2.7 Effect Verification

In order to determine the correlation between the T/G polymorphism at locus 926 in the promoter region of the ATP2A2 gene and an important phenotypic trait of chicken, 468 Wannan three-yellow chickens in the section 2.2 were taken as experimental materials, and the average daily feed intake (ADFI), average daily gain (ADG), metabolic body weight gain (MBW$^{0.75}$), feed conversion ratio (FCR), and RFI of 56-98 day-old chicken were counted. The 468 Wannan three-yellow chickens were genotyped by the genotyping method in the section 2.5, and results are shown in Table 3.

TABLE 3

| Genotyping results of individuals with different phenotypes | | | | | | | |
| --- | --- | --- | --- | --- | --- | --- | --- |
| | Genotype frequency | | | Gene frequency | | Chi-square test | |
| Locus | TT | TG | GG | T | G | $\chi^2$ | P value |
| T-926G | 0.066 | 0.404 | 0.530 | 0.268 | 0.732 | 0.391 | 0.822 |

Conclusion: Results of the chi-square test showed that genotypes of the experimental chicken population were in Hardy-Weinberg equilibrium (P>0.05).

2.8 Statistical Analysis

The correlation between the three genotypes and the chicken feed efficiency trait was analyzed by the least-squares analysis method in the SAS9.4 software, and analysis results of the correlation between the different genotypes and the trait are shown in Table 4.

TABLE 4

Analysis of the correlation between the chicken ATP2A2 genotypes and the chicken feed efficiency trait

| | Genotype | | |
| --- | --- | --- | --- |
| Trait | TT (n = 31) | TG (n = 189) | GG (n = 248) |
| ADFI (g/d) | 42.18 ± 3.65 | 41.82 ± 3.42 | 41.19 ± 3.41 |
| ADG (g/d) | 13.47 ± 1.65 | 13.39 ± 1.82 | 13.57 ± 1.67 |
| MBW$^{0.75}$ | 140.52 ± 7.79 | 141.72 ± 8.33 | 141.07 ± 9.18 |
| FCR (g/g) | 3.14 ± 0.37 | 3.16 ± 0.35 | 3.08 ± 0.23 |
| RFI (g/d) | 0.56 ± 0.80$^a$ | 0.05 ± 0.85$^b$ | −0.20 ± 0.92$^b$ |

Note:
Different low case letters in the same row indicate significant differences (P < 0.05).

Conclusion: It can be seen from the comparison of feed efficiency traits of individuals with different genotypes in Table 4 that, in terms of the RFI, GG, and TG individuals are significantly lower than TT individuals (P<0.05). Since the RFI is a negative selection trait, it can be known that individuals with the GG genotype have the highest feed conversion trait, individuals with the TG genotype have the medium feed conversion trait, and individuals with the TT genotype have the lowest feed conversion trait.

The above are merely several embodiments of the present disclosure. Although the descriptions of these embodiments are specific and detailed, these embodiments should not be construed as limiting the patent scope of the present disclosure. It should be noted that those of ordinary skill in the art can further make several variations and improvements without departing from the concept of the present disclosure, and these variations and improvements all fall within the protection scope of the present disclosure.

What is claimed is:

1. A method for identifying a chicken feed efficiency trait using a molecular marker, comprising the following steps:
   (1) extracting total DNA from venous blood of a chicken wing;
   (2) designing specific amplification primers with a sequence comprising a locus at which the molecular marker is located and upstream and downstream bases thereof as a target sequence, and using the specific amplification primers to conduct PCR amplification with the total DNA as a template to obtain an amplification product;
   (3) genotyping and sequencing the amplification product to obtain a molecular marker type of a chicken to be tested; and
   (4) determining the chicken feed efficiency trait based on the molecular marker type; wherein
   the molecular marker is an adenosine triphosphatase sarcoplasmic/endoplasmic reticulum $Ca^{2+}$ transporting 2 (ATP2A2) gene-based molecular marker and has the sequence set forth in SEQ ID NO: 1; and wherein
   if the molecular marker type of the chicken to be tested is a GG genotype, the chicken feed efficiency trait is at a high level;
   if the molecular marker type of the chicken to be tested is a TT genotype, the chicken feed efficiency trait is at a low level;
   if the molecular marker type of the chicken to be tested is a TG genotype, the chicken feed efficiency trait is at a medium level; and
   the chicken to be tested is a Wannan three-yellow chicken, and the chicken feed efficiency trait is determined according to residual feed intake (RFI);
   wherein sequences of the specific amplification primers are as follows:

SEQ ID NO: 2:
   forward primer:
   TTTAGCAGCGATGGATGT;
   and

SEQ ID NO: 3:
   reverse primer:
   GCGAGGAGGTATGAACTG.

2. The method for identifying a chicken feed efficiency trait using the molecular marker according to claim 1, wherein a method of the genotyping is as follows: cleaving the amplification product with a TatI restriction endonuclease to obtain a cleavage product, detecting the cleavage product by agarose gel electrophoresis, and allowing the genotyping according to an electrophoresis pattern, wherein if the cleavage product comprises:
   1 band, then the chicken feed efficiency trait is of a GG genotype;
   2 bands, then the chicken feed efficiency trait is of a TT genotype; and
   3 bands, then the chicken feed efficiency trait is of a TG genotype.

3. The method for identifying a chicken feed efficiency trait using the molecular marker according to claim 2, wherein the cleavage product is detected by agarose gel electrophoresis with a concentration of 2.0% or more.

* * * * *